Figure 1A:
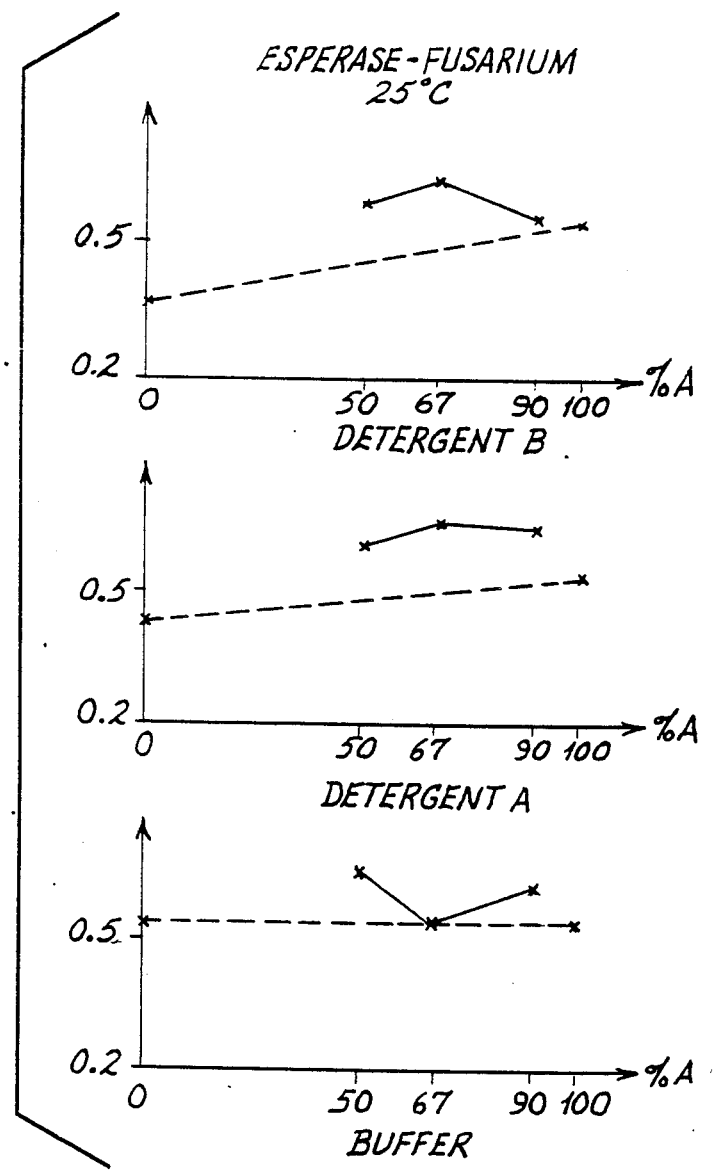
Figure 2A:
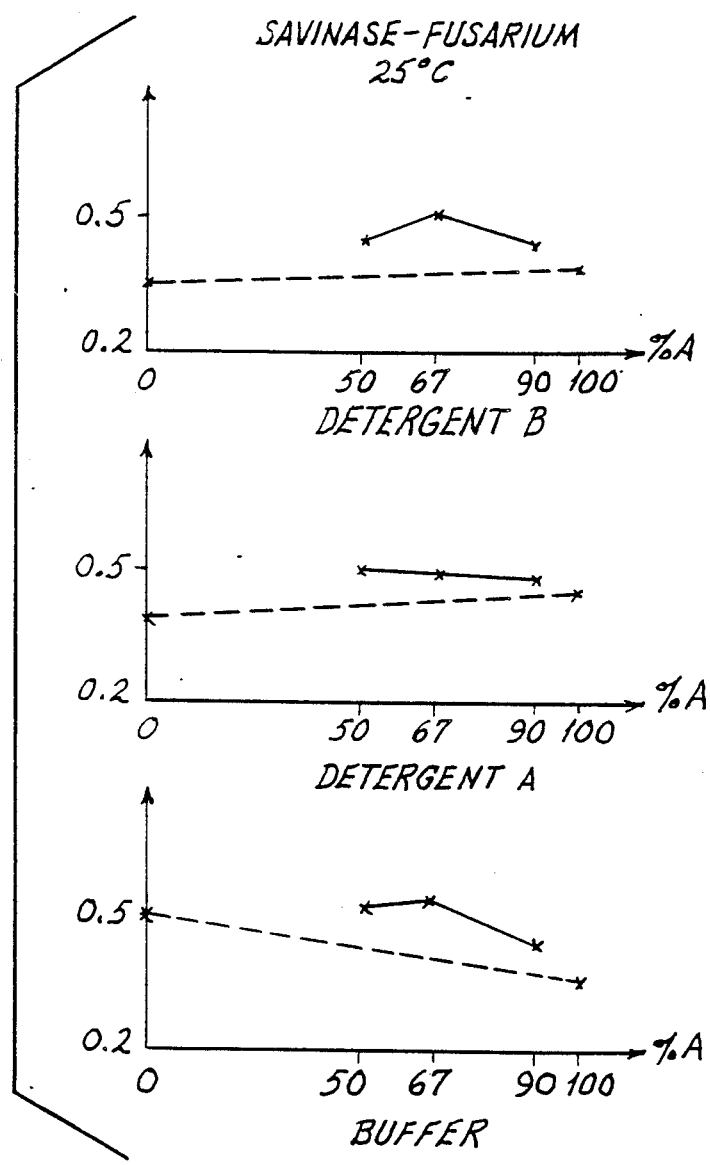
Figure 2B:
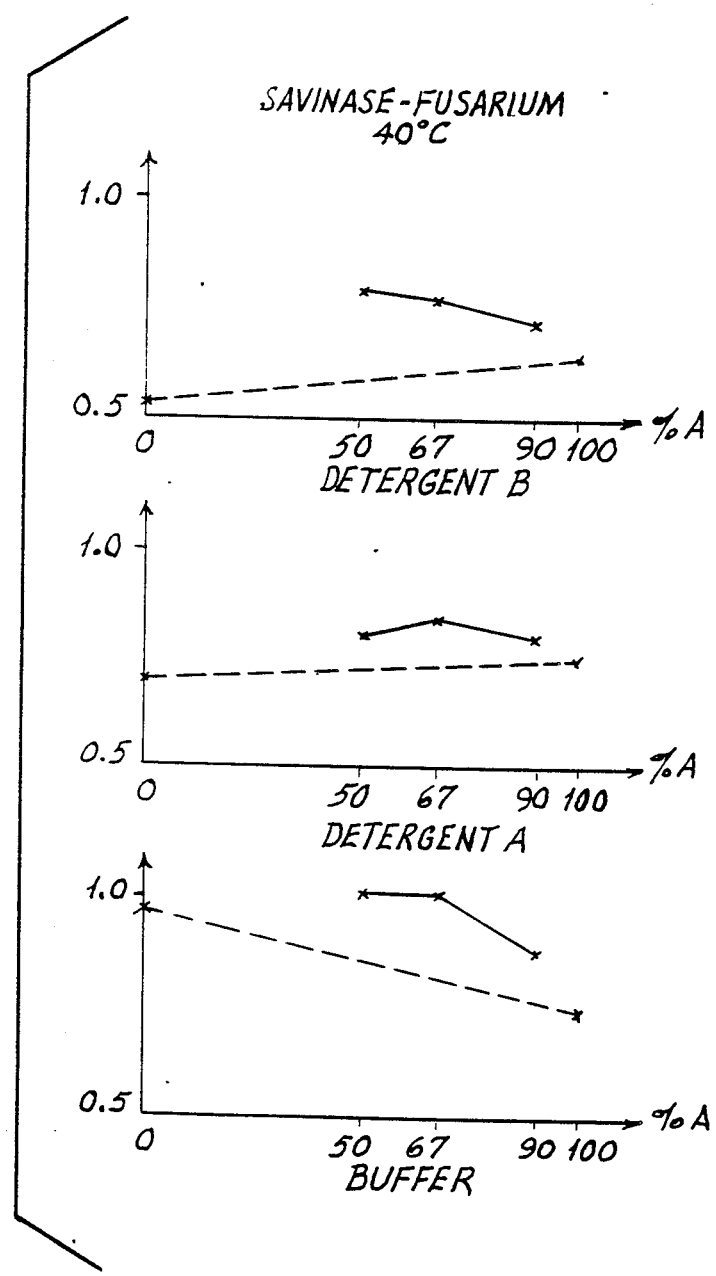
Figure 3B:
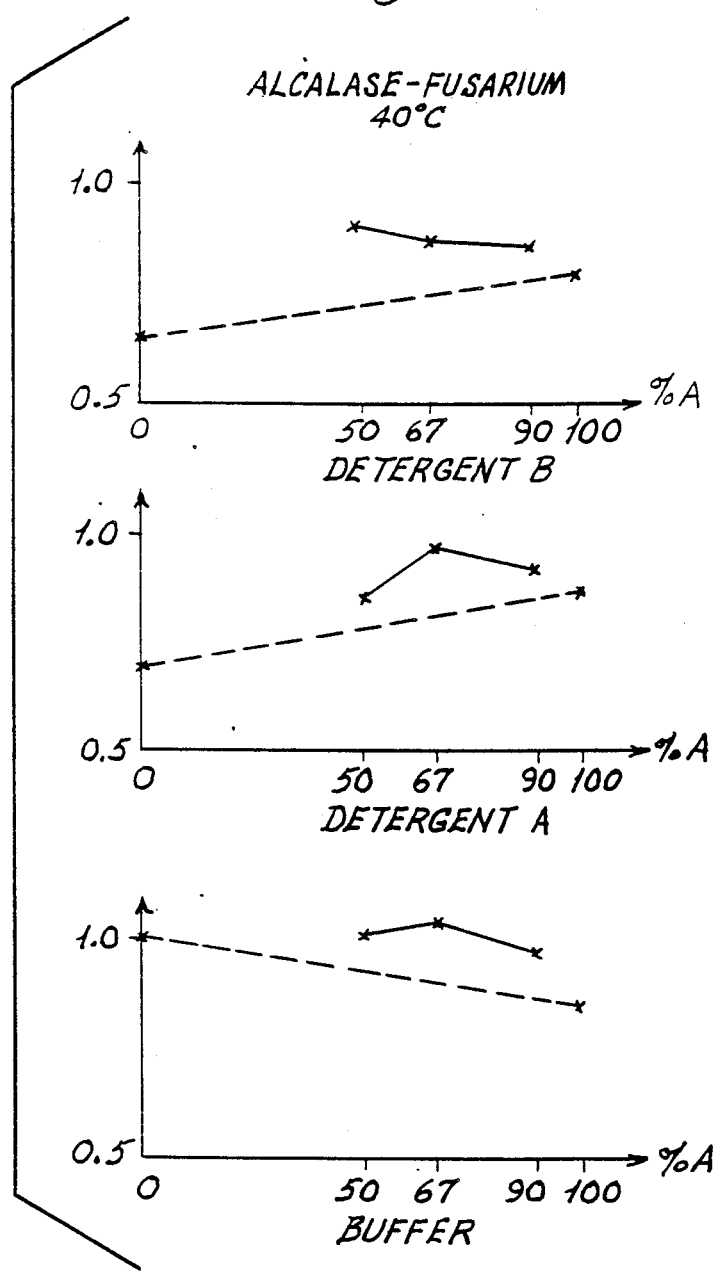

United States Patent [19]
Aaslyng et al.

[11] Patent Number: 4,927,558
[45] Date of Patent: May 22, 1990

[54] PROTEOLYTIC DETERGENT ADDITIVE AND COMPOSITIONS CONTAINING THE SAME

[75] Inventors: Dorrit A. Aaslyng, Roskilde; Georg W. Jensen, Bagsvaerd; Ib Schneider, Hellerup; Palle Schneider, Ballerup, all of Denmark

[73] Assignee: Novo Industri A/S, Bagsvaerd, Denmark

[21] Appl. No.: 223,787

[22] PCT Filed: Nov. 25, 1987

[86] PCT No.: PCT/DK87/00145
§ 371 Date: Aug. 31, 1988
§ 102(e) Date: Aug. 31, 1988

[87] PCT Pub. No.: WO88/03946
PCT Pub. Date: Jun. 2, 1988

[30] Foreign Application Priority Data
Nov. 25, 1986 [DK] Denmark .............................. 5640/86

[51] Int. Cl.$^5$ .................. C11D 3/386; C11D 7/42; C12N 9/50; C12N 9/58
[52] U.S. Cl. .................. 252/174.12; 252/DIG. 12; 435/222; 435/223; 435/264
[58] Field of Search .................. 252/174.12, DIG. 12; 435/222, 223, 265

[56] References Cited
U.S. PATENT DOCUMENTS

| | | |
|---|---|---|
| 3,519,570 | 7/1970 | McCarty .............................. 252/135 |
| 3,557,002 | 1/1971 | McCarty .............................. 252/89 |
| 3,652,399 | 3/1971 | Isono et al. .......................... 195/62 |
| 3,939,040 | 2/1976 | Monsheimer et al. ................. 195/6 |
| 3,966,551 | 6/1976 | Monsheimer et al. ................. 195/6 |
| 3,986,926 | 10/1976 | Monsheimer et al. ................. 195/6 |
| 4,511,490 | 4/1985 | Stanislowski et al. .......... 252/174.12 |
| 4,636,222 | 1/1987 | Pfleiderer et al. ................... 8/94.16 |

FOREIGN PATENT DOCUMENTS 2004328 5/1983 Denmark .

OTHER PUBLICATIONS

Chemical Abstracts, vol. 95, 1981, Abstract No. 22917t, Sharma, O. P. et al., "Studies on in vitro Production of Proteolytic Enzymes by Some Leather-Deteriorating Fungi".

Primary Examiner—Paul Lieberman
Assistant Examiner—A. Beadles-Hay
Attorney, Agent, or Firm—Morris Fidelman; Franklin D. Wolffe

[57] ABSTRACT

Combinations of alkaline Bacillus protease with alkaline fungal or actinomycete protease show improved detergency. Proteases obtainable from Fusarium sp. or Paecilomyces sp. (fungal) and Nocardiopsis sp. (actinomycete) are preferred.

14 Claims, 14 Drawing Sheets

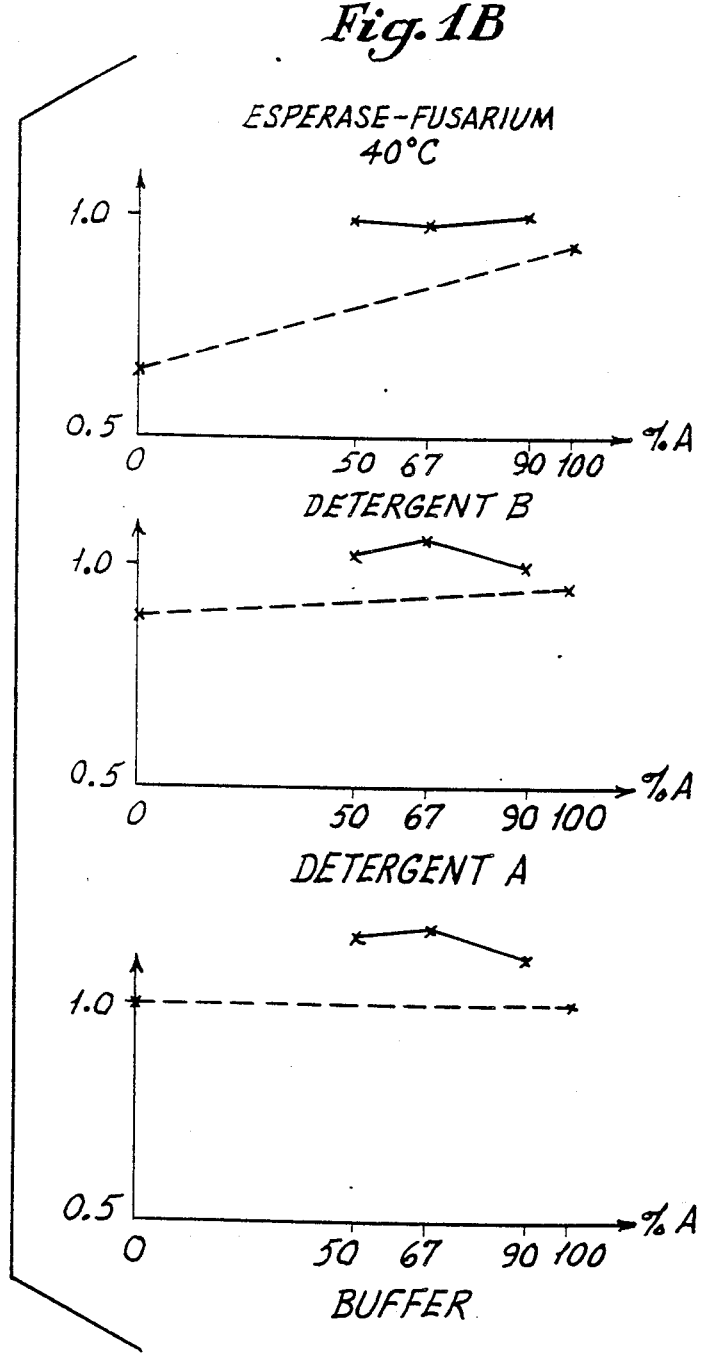

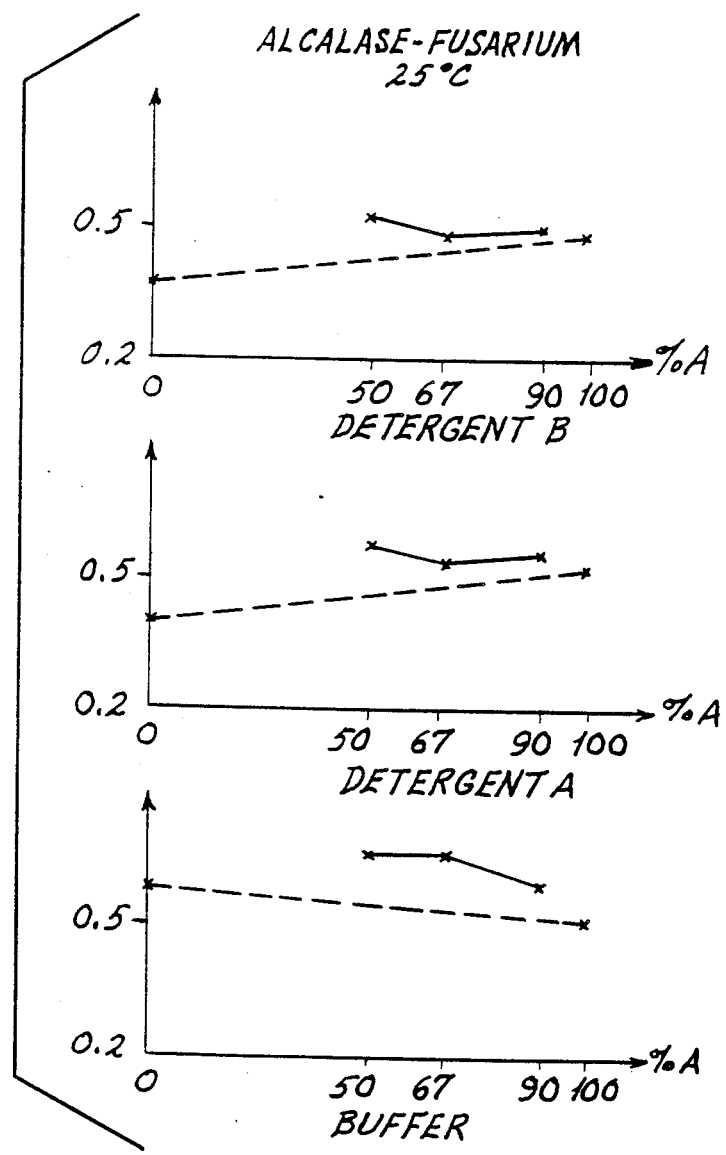

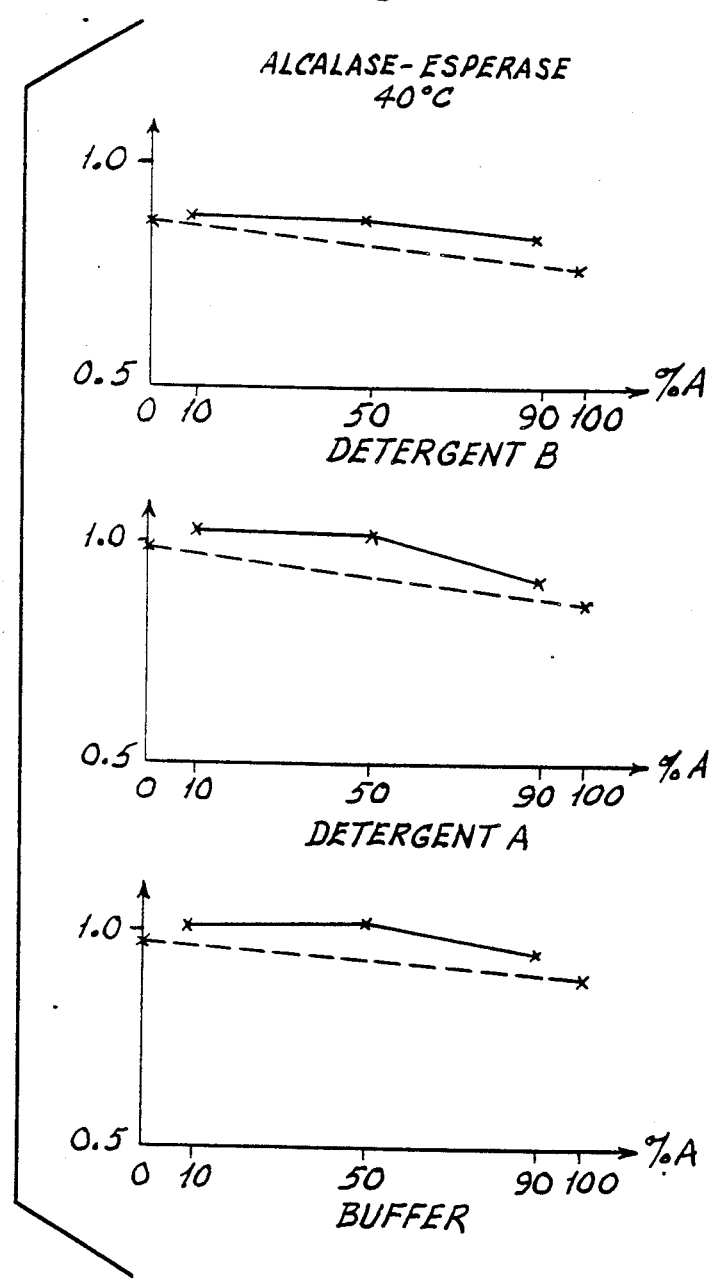

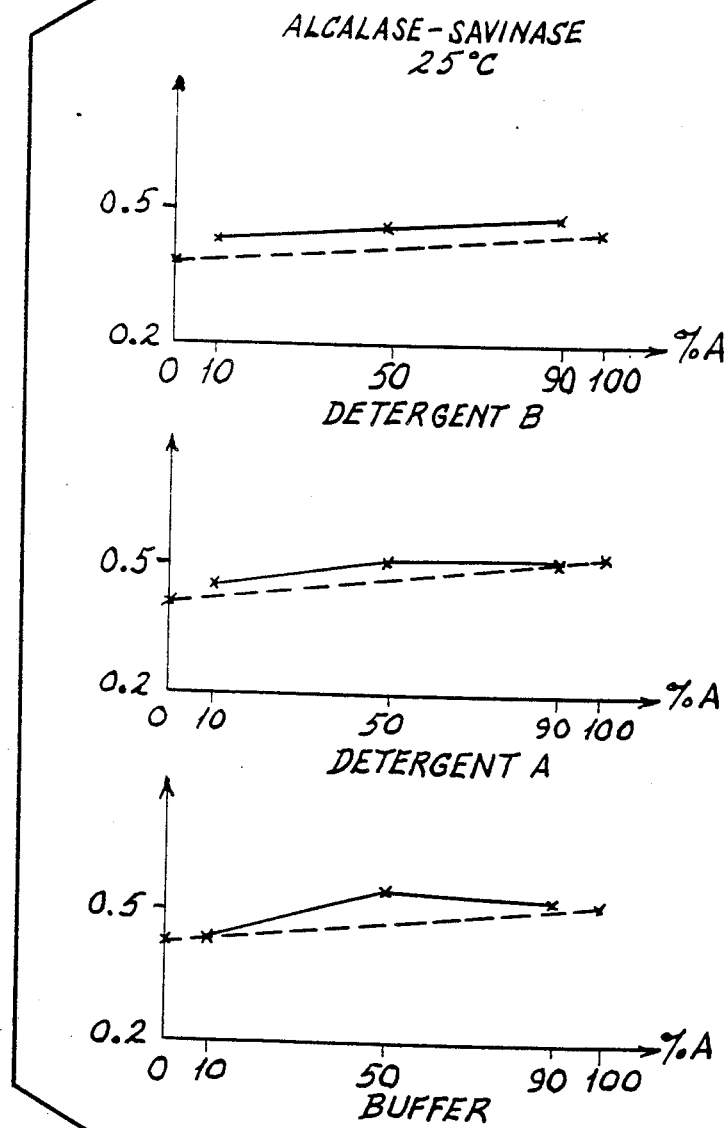

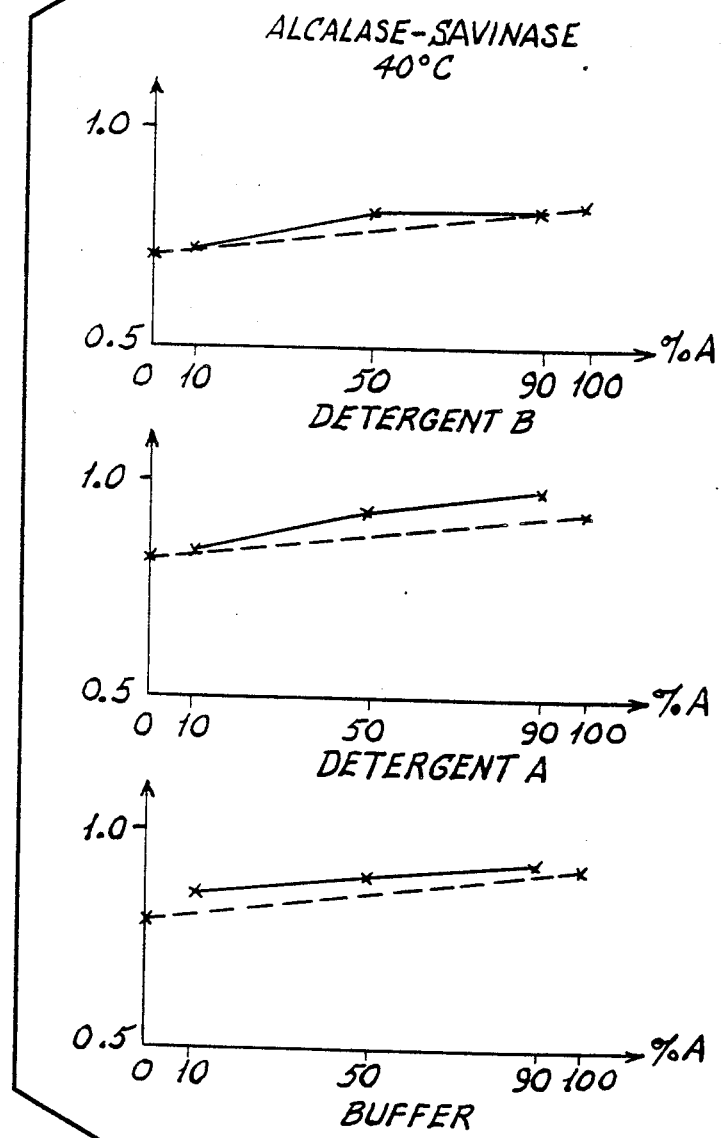

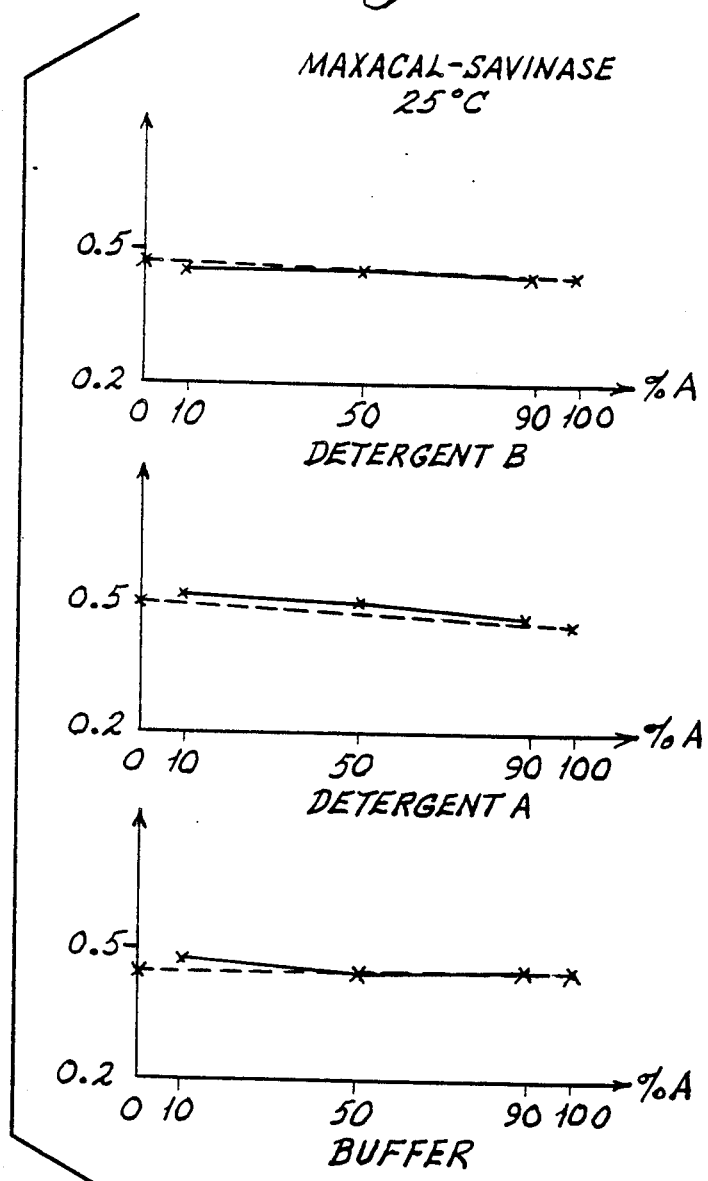

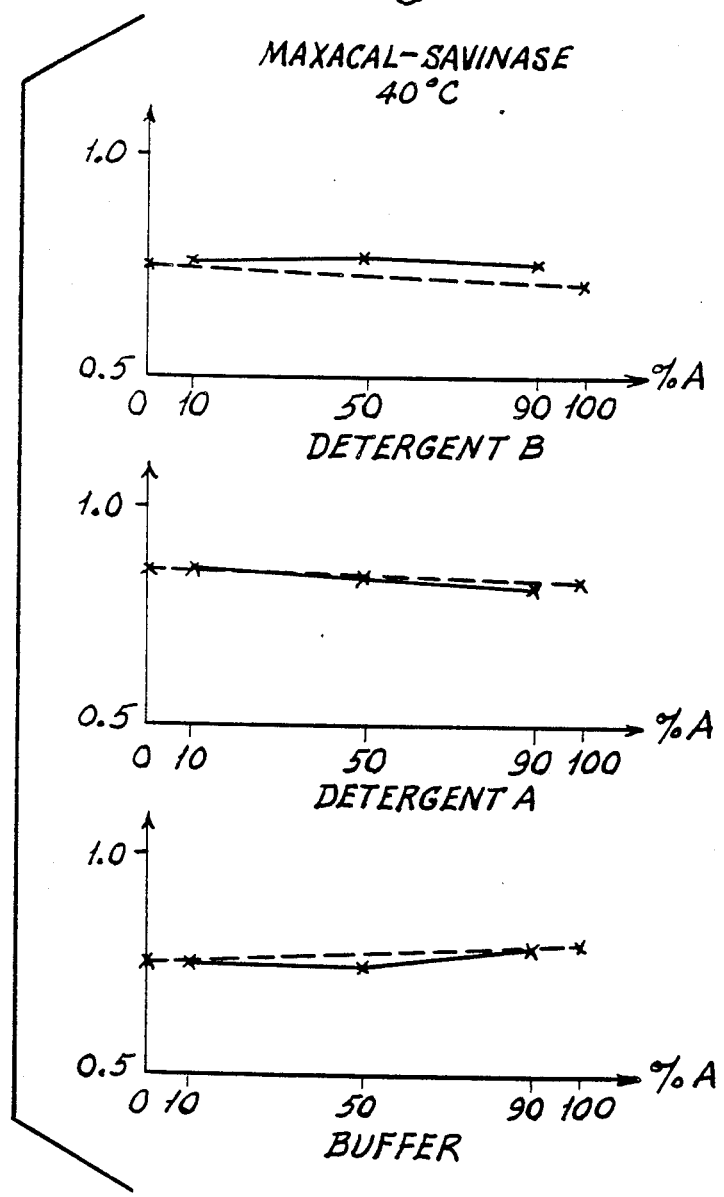

PROTEOLYTIC DETERGENT ADDITIVE AND COMPOSITIONS CONTAINING THE SAME

This invention concerns a proteolytic detergent additive comprising a combination of alkaline proteases, a cleaning agent and a washing method.

TECHNICAL FIELD

The field comprising enzymatic additives in detergents has been rapidly growing during the last decades. Reference is made to e.g. the article "How Enzymes got into Detergents", vol. 12, Developments in Industrial Microbiology, a publication of the Society for Industrial Microbiology, American Institute of Biological Sciences, Washington, D.C. 1971, by Claus Dambmann, Poul Holm, Villy Jensen and Mogens Hilmer Nielsen, and to P. N. Christensen, K. Thomsen and S. Branner: "Development of Detergent Enzymes", paper presented on 9 October 1986 at the 2nd World Conference on Detergents held in Montreux, Switzerland.

In particular, alkaline proteases produced by cultivation of strains of *Bacillus sp.* in suitable nutrient media are widely used in detergent compositions. Examples of such commercial protease products are ALCALASE ®, ESPERASE ®, ESPERASE ® and SAVINASE ®, all supplied by NOVO Industri A/S, Denmark. These and similar enzyme products from other commercial sources are active in detergent solutions, i.e. at pH values in the range of from 7 to 12 and in the presence of sequestering agents, surfactants and bleaching agents, such as sodium perborate. ALCALASE ® is produced by strains of the species *Bacillus licheniformis*. ESPERASE ® and SAVINASE ® are obtained by cultivation of strains of alkalophilic Bacilli according to U.S. Pat. No. 3,723,250.

Large efforts have been devoted over the past two decades to developing proteases with improved detergency, that can yet be produced economically. These efforts have concentrated on alkaline proteases from *Bacillus sp.*, like those now used in the detergent industry. Besides showing good detergency, proteases in this group can in general be produced efficiently as techniques for strain improvement and submerged fermentation of *Bacillus sp.* are well developed. However, as large efforts have already been made, it has proven increasingly difficult to find better proteases in this well-explored area.

Proteases from other microorganisms, such as fungi and actinomycetes, have also been studied. As an example, U.S. Pat. No. 3,652,399 discloses that alkaline protease from the fungus *Fusarium oxysporum* has high activity at pH values in the range from 8 to 11.5 and is effective for use in a detergent. As another example, German Democratic Republic patent publication DD-2,004,328 discloses an alkaline protease from the actinomycete *Nocardiopsis dassonvillei* with activity in the range pH 6–10; examples of this specification demonstrate that it is effective for washing.

Some of these proteases show good detergency, but they are in general difficult to produce economically. Today, fungal and actinomycete proteases are not available at comparable prices to Bacillus proteases, and it is believed that they are not used commercially in detergents.

It is the object of this invention to provide a proteolytic detergent additive comprising a combination of two or more proteases, showing improved detergency. Surprisingly, it has been found that this can be obtained by a combination of one or more Bacillus proteases with one or more fungal or actinomycete proteases, whereby the Bacillus protease or proteases provides from 50 to 95% of total proteolytic activity.

BACKGROUND ART

In 1981 a detergent was sold on the European market with an enzymatic additive comprising a mixture of ALCALASE ® and ESPERASE ®, i.e. two alkaline proteases from *Bacillus sp.*

Also, it appears from Osaka Shiritsu Daigaku Seikatsu Kagakubu Kiyo 23, (1975), page 69, that in a washing process it is sometimes more effective to use a mixture of a neutral protease and an alkaline protease. No data or further details of the combined effect are provided.

Also, U.S. Pat. No. 4,511,490 describes a cooperative mixture of two proteases. The exemplified proteases are all alkaline proteases from *Bacillus sp.* The effect is only demonstrated by measuring hydrolysis of a casein solution in the absence of detergent. It is speculated that the protease combination may provide improved detergency, but data from washing tests are not provided. The highest activity was found at a mixing ratio of the two proteases on activity basis from approx. 1:2 to approx. 2:1.

Further, Japanese examined patent application publication 61-19,679 describes the use in a detergent of a combination of two proteases. The exemplified combination uses alkaline proteases from *Bacillus sp.* The data from washing tests do not show any improved detergency over the use of a single protease, but merely that the effect extends over a broader temperature range than that of each protease alone. The mixing ratio of the two proteases is 1:1 on activity basis.

Thus, a detergent additive comprising two alkaline proteases from *Bacillus sp.* for detergents is known, but data showing improved detergency have not been published. Examples later in this specification demonstrate that, in fact, the detergency of such mixtures is only slightly better than that of the single proteases. Detergent additive comprising an alkaline bacterial protease together with an alkaline fungal or actinomycete protease has not previously been described.

The use of alkaline bacterial and fungal proteases together for treatment of leather is disclosed in West German patent publications DE-2,301,591A, DE-2,307,603A, DE-2,308,967A and DE-2,321,629A. The effects obtained therein are unhairing, bating and softening of leather, and the chemical environment includes reducing sulfur compounds; such as sulfide, mercaptans or sulfite, but does not include surfactant or other common detergent components.

SUMMARY OF THE INVENTION

This invention provides a proteolytic detergent additive comprising a combination of at least two alkaline proteases, of which at least one is a protease obtainable from *Bacillus sp.* and at least one is a fungal or actinomycete protease. Preferably, the mixing ratio is such that the Bacillus protease provides 50–95% of the total proteolytic activity (measured in CPU to be described later), preferably 70–95%. In a preferred embodiment, the detergency of the combination is greater than that expected from detergency of each protease, preferably at least 20% greater, and most preferably at least 40% greater.

In the comparison of detergency, washing tests may be done by the method given in Example 8 of this specification, using any set of conditions given therein.

Alternatively, washing tests may be done in a Terg-o-Tometer using water hardness and detergent composition and dosage as in any of the examples of this specification. Washing conditions may be 10, 20 or 40 minutes at 15°, 25°or 40° C. The type of soiled swatch may be heat-denatured blood swatches, surface-denatured blood swatches, heat-denatured spinach swatches or EMPA 116, all described later in this specification. Detergency may be evaluated by reflectance or protein removal and be expressed as Δ R (% reflectance) or PR (% protein removal) as detailed later in this specification. The protease combination should be dosed at 0.05 or 0.1 CPU/l. Comparative washing tests should be made with the single proteases at the same total dosage. Comparison of detergency of the protease combination may be made either with that of pure Bacillus protease (as this contributes the largest activity), or with the larger of detergencies of each protease, or with a weighted average (linear interpolation) of the detergencies of each protease.

In a preferred embodiment the alkaline proteases have optimum activity towards casein (by the CPU method to be described later) at a pH above 9. Such proteases are suitable for use with powder detergent as the pH in solution is usually above 9.

In preferred embodiments, the detergent additive comprises a Bacillus protease obtainable from *B. licheniformis* or the alkalophilic *Bacillus sp.* disclosed in U.S. Pat. No. 3,723,250. The latter proteases are characterized by being of the serine type and by showing optimal proteolytic activity at a pH value above about 9 and retaining 80 to 100 percent of maximum proteolytic activity at pH 12, said activities being measured against hemoglobin by the Anson method. All these proteases have good detergency and can be produced economically, and are therefore widely used commercially.

In preferred embodiments, the detergent additive comprises a fungal or actinomycete protease obtainable from *Paecilomyces sp., Fusarium sp.* or *Nocardiopsis sp.*, most preferably from *P. marquandii, F. oxysporum* or *N. dassonvillei*. These proteases show good detergency when combined with Bacillus protease.

In a preferred embodiment of this invention, the detergent additive is provided as a non-dusting granulate, prepared by any method known in the art, e.g. according to GB Pat. No. 1,362,365 or U.S. Pat. No. 4,106,991. The proteases may be mixed before or after granulation, i.e. the enzyme preparation may consist of granules each containing two or more proteases, or it may be a mixture of granules containing each protease. A non-dusting granulate is the most convenient form for adding to powder detergent.

In another preferred embodiment, the detergent additive is provided as a liquid with an enzyme stabilizer, such as propylene glycol or other agents known in the art to stabilize proteases. This is convenient for adding to liquid detergent.

In a preferred embodiment of the detergent additive of this invention, the total protease activity is between 0.1 and 10 CPU/g, preferably 0.5 to 5 CPU/g. When this is added to a cleaning agent in an amount of 0.05% to 5%, preferably 0.1 to 2%, and the cleaning agent is used in a concentration of 0.5 to 20 g/l, a suitable protease activity, typically 0.02 to 0.5 CPU/l, will be generated.

Another aspect of this invention provides a cleaning agent composition containing a combination of at least two proteases as described above. The cleaning agent may be a powder detergent or a liquid detergent. The two proteases may be added as separate additives to the cleaning agent, or they may be added in the form of a combined additive such as the enzyme preparation described above.

In a preferred embodiment the protease activity of the cleaning agent is from 0.001 to 0.08 CPU/g, preferably b 0.003 to 0.012 CPU/g. When this is used at a concentration of 0.5 to 20 g/l, a suitable protease activity, typically 0.02 to 0.5 CPU/l is generated.

Still another aspect of the invention provides a washing method using at least two proteases together. The two proteases may be added in the form of the enzymatic cleaning agent described above, or they may be added separately into the washing process.

DETAILED DISCLOSURE OF THE INVENTION

Assay for Proteolytic Activity

The proteolytic activity was determined by the well known Anson hemoglobin method, cfr. *Journal of General Physiology*, 22, 79–89 (1959). One Anson unit is the amount of proteolytic enzyme digesting hemoglobin at a pH value of 9.0 and a temperature of 25° C. during a reaction time of 10 minutes with such an initial velocity that per minute there is formed such an amount of split products which cannot be precipitated with trichloracetic acid that these split products give the same colour with phenol reagent as does one milliequivalent of tyrosine.

The proteolytic activity was also determined with casein as the substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5. A 2% (w/v) solution of casein (Hammarsten, supplied by Merck A.G., West Germany) was prepared with the Universal Buffer described by Britton and Robinson (Journ. Chem. Soc. 1931, p. 1451) adjusted to pH 9.5.

Two ml of substrate solution is preincubated in a water bath for 10 minutes at 25° C. One ml of enzyme solution is added. After 30 minutes of incubation at 25° C. the reaction is terminated by the addition of a stopping agent (5 ml of a solution containing trichloroacetic acid (17.9 g), sodium acetate (29.9 g), and acetic acid (19.8 g), filled up to 500 ml with deionized water). A blank is prepared in the same manner as the test solution, except that the stopping agent is added prior to the enzyme solution.

The reaction mixtures are kept for 10 minutes in the water bath, whereupon they are filtered through Whatman ® 42 paper filters.

Primary amino groups are determined by their colour development with o-phthaldialdehyde (OPA).

Disodium tetraborate decahydrate (7.62 g) and sodium dodecylsulfate (2.0 g) is dissolved in 150 ml of water. OPA (160 mg) dissolved in 4 ml of methanol is then added together with 400 μl of beta-mercaptoethanol, whereafter the solution is made up to 200 ml with water.

To the OPA reagent (3 ml) is added 400 μl of the above-mentioned filtrates with mixing. The optical density (OD) at 340 nm is measured after about 5 minutes.

The OPA test is also performed with a serine standard containing 10 mg of serine in 100 ml of Britton-Robinson buffer (pH 9.5). The buffer is used as a blank.

The protease activity was calculated from the optical density measurements by means of the following formula:

$$CPU/ml = \frac{(OD_t - OD_b) \times C_{ser} \times Q}{(OD_{ser} - OD_B) \times MW_{ser} \times t_i}$$

wherein $OD_t$, $OD_b$, $OD_{ser}$ and $OD_B$ is the optical density of the test solution, blank, serine standard, and buffer, respectively, $C_{ser}$ the concentration of serine in mg/ml in the standard, $MW_{ser}$ the molecular weight of serine, Q the dilution factor for the enzyme, and $t_i$ the incubation time.

Washing equipment

Washing trials were done in a Terg-o-Tometer as described in Jay C. Harris: Detergency Evaluation and Testing, Interscience Publishers Ltd., 1954, pp. 60–61.

Soiled swatches

Three kinds of soiled swatches are used in the washing tests. These are prepared as follows:

Heat denatured blood swatches:

White textile (50% polyester, 50% cotton) was desized with amylase (BAN Novo) and dried.

The swatches were cut into pieces (10×20 cm), immersed into bovine blood (with citrate to prevent coagulation) and squeezed between 2 rollers. Then they were dried in a tumbler (60° C.).

The swatches were denatured in 60° C. hot water for 8 min, rinsed in cold water and dried in a tumbler (60° C.).

Surface denatured blood swatches:

White textile (100% cotton) was desized with amylase (BAN Novo) and dried.

The swatches were cut into pieces (10×20 cm), immersed into bovine blood (with citrate to prevent coagulation) and airdried.

The swatches were stored at room temperature for 2 weeks to ensure, that the blood had adhered to the textile. Then they were kept at −18° C. until use.

Heat denatured spinach swatches:

White textile (100% cotton) was desized with amylase (BAN Novo) and dried.

The swatches were cut into pieces (10×20 cm), immersed into spinach juice and squeezed between 2 rollers. Then they were dried in a tumbler (60° C.). This was repeated twice.

The denaturation was carried out as described above.

Detergent solution

Except where otherwise noted, 5 g/l solution with pH approx 9.5 was prepared by dissolving the following in water of 9° german hardness:

| | | |
|---|---|---|
| LAS (Nansa S 80) | 0.40 | g/l |
| AE (Berol 065) | 0.15 | — |
| Soap | 0.15 | — |
| STPP | 1.75 | — |
| Sodium silicate | 0.40 | — |
| CMC | 0.05 | — |
| EDTA | 0.01 | — |

-continued

| | | |
|---|---|---|
| Na$_2$SO$_4$ | 2.10 | — |

Washing procedure

Except where otherwise noted, washing trials are done in a Terg-o-Tometer with 100 rpm, using swatches of 9.0 cm×5.5 cm (approx. 1 g) in 100 ml of detergent solution per swatch and the enzyme dosage indicated in each example.

After washing the swatches are rinsed for 15 minutes in running tap water and air dried. Then reflectance is measured at 460 nm in an Elrepho reflectometer and/or residual protein is measured by the method described below.

The results are expressed as differential reflectance $\Delta R = R - R_o$ or differential protein removal $\Delta PR = PR - PR_o$, where $R_o$ and $RP_o$ are the values obtained by washing with detergent without protease at the same conditions.

Determination of residual protein on cotton swatches

The swatches are cut into 1 cm×1 cm pieces. An amount corresponding to 0.5–0.8 mg of protein is weighed out and are placed in Hagedorn vessels. 4 ml of the above mentioned detergent solution is added. Then, 2 ml of protease solution containing Esperase ® (Novo Industri A/S, Denmark) in a concentration of 10 CPU/l.

After addition of the Esperase ® the mixture is incubated for 4 hours in a shaking bath of 40° C.

At the end of incubation the reaction is stopped by adding 2 ml of 10% acetic acid.

Blanks are made of 2 ml detergent solution and 1 ml Esperase ® and stopped with 1 ml 10% acetic acid.

After incubation the reaction mixtures are filtered through Whatman 42 filters. 400 μl of filtrate is mixed with 3 ml of OPA Reagent (prepared as indicated above), and the optical density at 340 nm is measured after about 5 minutes.

The OPA test is also performed with a serine standard containing 10 mg of serine in 100 ml of Britton-Robinson buffer (pH 9.5). The buffer is used as a blank.

The protein amount (as serine equivalent) is calculated by the following formula:

$$\text{mg serine/g swatch} = \frac{OD_{test} \times 0.10 \times 8}{OD_{serine} \times a}$$

where a is the weight of swatch (g). By comparing to the protein amount of the swatches before washing, % protein removal ($\Delta PR$) is calculated.

Fungal and actinomycete proteases

Strains used for preparing proteases for use in this invention were deposited for the patenting under the terms of the Budapest Treaty as indicated below:

| Species | Strain No | Deposit No | Deposit date |
|---|---|---|---|
| *Paecilomyces marquandii* | 2R-126 | NRRL 18048 | Feb. 18, 1986 |
| *Nocardiopsis dassonvillei* | M58-1 | NRRL 18133 | Nov. 13, 1986 |
| *Fusarium oxysporum* | J 79 | DSM 2672 | June 6, 1983 |

NRRL indicates Agricultural Research Culture Collection, 1815 North University Street, Peoria, Illinois 61604, USA. DSM indicates Deutsche Sammlung von Mikroorganismen, Gesellschaft für Biotechnologische Forschung mbH, Grisebachstr. 8, 3400 Göttingen, Fed. Rep. of Germany.

Fusarium protease as used in examples of this specification indicates protease prepared according to U.S. Pat. No. 3,652,399, using strain J79 (DSM 2672).

Nocardiopsis protease as used in examples of this specification indicates protease prepared according to German Democratic Republic patent publication DD-2,004,328, using strain M58-1.

Preparation of protease from *Paecilomyces marquandii*

Two batches of this protease were prepared for use in the examples. One batch was prepared as follows:

*Paecilomyces marquandii* strain NRRL 18048 was cultivated in a medium consisting of the following (grams/liter):

|   |   |   |
|---|---|---|
| Maltodextrin | 20 |
| Soybean Flour | 20 |
| $K_2HPO_4$ | 9 |
| $CaCO_3$ | 5 |
| Yeast Extract | 2 |
| Pluronic ® 25R2 | 1 |

After autoclaving, the pH was adjusted to 9.2 by addition of $Na_2CO_3/NaHCO_3$ buffer to a final concentration of 0.1M. The culture was incubated at 250 rpm, 30° C., for 24 hours. After this growth period, the culture (600 ml) was used to inoculate a fermenter containing 10 liters of the following medium (grams/liter):

|   |   |
|---|---|
| Glucose | 50 |
| Soybean Flour | 100 |
| $K_2HPO_4$ | 5 |
| $CaCO_3$ | 5 |

After sterilization, the medium was adjusted to pH 8.2 with 2M $Na_2CO_3$. The pH fell to about 7.0 during the early stages of growth in the fermenter. The temperature was controlled at 30° C. initially, and was lowered to 25° C. when the pH began to rise above 7.0. From this point on, pH was controlled not to fall below 7.0 by addition of KOH or $Na_2CO_3$ and not to exceed 7.6 by addition of $H_3PO_4$. Pluronic ® was used to control foam. Agitation and aeration were increased as $O_2$ demand increased; the fermenter was operated at maximum oxygen transfer rate by 24 hours. After 120 hours, protease titer was determined using the Anson assay method, a value of 25 Anson units/liter being indicated.

The culture broth was filtered to become the Paecilomyces protease employed in Example 7.

A second batch of protease was prepared as follows:

| Organism: | | 2R-126 (NRRL 18048) | |
|---|---|---|---|
| Fermenter size: | | 550 l | |
| | | Seed fermenter | Main fermenter |
| Soy bean meal | g/l | 20 | 100 |
| Yeast extract | — | 2 | 2 |
| $KH_2PO_4$ | — | 8 | 5 |
| Potato starch | — | 20 | |
| $CaCO_3$ | — | 4,8 | 5 |
| Pluronic ® | ml/l | 0,20 | 0,27 |
| Termamyl ® 60 L | — | | 0,04 |

| -continued | | |
|---|---|---|
| (Heat Stable α-amylase) | | | pH was adjusted before inoculation to 9.2 by addition of $Na_2CO_3$.

A 30% glucose solution was fed continuously to the main fermenter during the fermentation. The total amount of glucose fed to the fermenter was 143 g/l of initial volume.

| Inoculation volume of main fermenter: | | 10% vol/vol |
|---|---|---|
| Fermentation time: | (a) seed culture | 62 hours |
| | (b) main culture | 113 hours |
| Fermentation parameters: | | |
| | Seed fermenter | Main fermenter |
| Temperature | 30° C. | 25–30° C. |
| Air flow vol/vol/min | 0.8 | 1.0 |
| Pressure ato | 0.5 | 0.5 |
| Impeller speed rpm. | 140–300 | 400–420 |
| pH | 8.4–9.4 | 7.6–9.0 |

The protease activity of the culture broth was 3.5 AU/kg

The recovery process of the protease was as follows:
(1) The culture broth from the fermentation was filtered on a drum filter (pH 7.5)
(2) The filtrate was blank filtered
(3) The filtrate was UF-concentrated
(4) The UF concentrate was blank-filtered
(5) Thereafter microorganisms were filtered off
(6) The enzyme was salted out and dried under vacuum The activity of the product was measured to be 0.45 CPU/g.

This preparation was designated PDF-29 and was employed in Examples 1, 2, 5, and 6.

EXAMPLE 1

This example illustrates the invention by comparing the washing effect of Savinase ®, both according to this invention and to prior art. In the experiment, heat-denatured blood swatches were washed at 25° C. for 20 minutes at a total protease dosage of 0.1 CPU/l. In each case, results by use of the second protease alone at 0.1 CPU/l are shown in parentheses.

| Protease dosage (CPU/l) | Reflectance (ΔR) |
|---|---|
| 0.1 Savinase | 7.6 |
| This invention | |
| 0.075 Savinase + 0.025 Nocardiopsis | 10.3 (1.5) |
| 0.075 Savinase + 0.025 Fusarium | 10.7 (6.7) |
| 0.075 Savinase + 0.025 Paecilomyces | 10.1 (4.6) |
| Prior art | |
| 0.075 Savinase + 0.025 Alcalase | 9.1 (1.1) |
| 0.075 Savinase + 0.025 Esperase | 7.3 (5.3) |

EXAMPLE 2

This example shows the effect of mixing ratio of two proteases on washing performance. Two combinations according to this invention were used, and one prior art combination was included for comparison. Conditions were as in Example 1.

| | ΔR at each dosage in CPU/l | | | | |
|---|---|---|---|---|---|
| Protease A + Protease B | 0.1A | 0.075A + 0.025B | 0.05A + 0.05B | 0.025A + 0.075B | 0.1B |
| This invention | | | | | |
| Savinase + Paecilomyces | 7.6 | 10.1* | 8.4* | 7.1** | 4.6 |
| Savinase + Fusarium | 7.6 | 10.9* | 10.6* | 7.9** | 6.7 |
| Prior art | | | | | |
| Savinase + Esperase | 7.6 | 7.3 | 6.9 | 5.5 | 5.3 |

*Protease combination according to this invention
**Protease combination outside the scope of this invention, for comparison.

In each series above, the total protease dosage was kept constant at 0.1 CPU/l, and the ratio between protease A and B was varied. With the prior-art combination no improvement over pure Savinase is seen, but surprisingly the combinations of this invention show a marked improvement by mixing a small amount of fungal protease with the bacterial protease.

EXAMPLE 3

Heat-denatured blood swatches were washed for 20 minutes at 25° C., and protein removal was measured, as follows:

| Protease dosage (CPU/l) | | ΔPR |
|---|---|---|
| Savinase | 0.1 | 24.4 |
| Fusarium | 0.1 | 23.3 |
| Savinase + Fusarium | 0.075 + 0.025 | 30.5 |

EXAMPLE 4

The invention is illustrated through washing tests with spinach swatches. Conditions were 10 minutes at 25° C. with a total protease dosage of 0.1 CPU/l, and reflectance was measured.

| | | ΔR at each CPU/l | | |
|---|---|---|---|---|
| Protease A | Protease B | 0.1A | 0.1B | 0.075A + 0.025B |
| Alcalase | Nocardiopsis | 6.5 | 6.9 | 7.3 |
| Alcalase | Fusarium | 6.5 | 7.7 | 8.1 |
| Savinase | Fusarium | 8.2 | 8.4 | 9.8 |

EXAMPLE 5

Here the invention is illustrated through its action on surface denatured blood swatches. Protease combinations according to this invention were compared with prior-art combinations. Washing conditions were 10 minutes at 15° C., and reflectance was measured.

| | | ΔR at each CPU/l | | | | |
|---|---|---|---|---|---|---|
| Protease A | Protease B | 0.1B | 0.05A + 0.05B | 0.075A + 0.025B | 0.09A 0.01B | 0.1A |
| This invention: | | | | | | |
| Savinase | Fusarium | 4.2 | 3.7 | 3.3 | 4.3 | 2.7 |
| Savinase | Paecilomyces | 3.5 | 2.7 | 3.4 | 4.2 | 2.7 |
| Prior art: | | | | | | |
| Savinase | Alcalase | 2.2 | 2.0 | 1.8 | 1.8 | 2.7 |
| Savinase | Esperase | 2.2 | 1.1 | 2.4 | 1.9 | 2.7 |

EXAMPLE 6

Surface-denatured blood swatches were washed for 10 minutes at 15° C., and protein removal was measured. Protease combinations of this invention were compared with prior-art combinations, all involving Esperase ®. Results by washing with the second protease alone at 0.1 CPU/l are indicated in parentheses.

| Protease dosage (CPU/l) | ΔPR |
|---|---|
| 0.1 Esperase | 28 |
| This invention | |
| 0.09 Esperase + 0.01 Fusarium | 31 (31) |
| 0.09 Esperase + 0.01 Paecilomyces | 31 (17) |
| 0.09 Esperase + 0.01 Nocardiopsis | 34 (29) |
| Prior art | |
| 0.09 Esperase + 0.01 Alcalase | 24 (28) |
| 0.09 Esperase + 0.01 Savinase | 28 (20) |

EXAMPLE 7

Washing tests were performed in a Terg-o-Tometer for 10 minutes at 15° C. with EMPA 116 test fabric swatches, 5 cm×5 cm (cotton soiled with blood, milk and carbon black), supplied by Eidgenossische Materialprufungs-und Versuchanstalt, Sankt Gallen, Switzerland in the presence of Tide without phosphate (0.15% w/v).

The cleaning ability of the proteases was measured by reflectance change (ΔR) comparing the reflectance values of enzyme-washed test swatches to swatches washed without enzyme. Reflectance values were read with the aid of a Gardiner Reflectometer XL 800 (Bethesda, MD).

ALCALASE ® was either used alone (0–0.6 AU/l) or in mixtures with the Paecilomyces protease (0.4 AU/l of ALCALASE ® plus 0.05–0.4 AU/l Paecilomyces protease).

The results are shown in the table below. The addition of the fungal protease does result in reflectance changes (superior wash efficacy) significantly greater than those obtained by ALCALASE ® alone at the same total dosage.

| ALCALASE ® Dose (AU/l) | *Paecilomyces marquandii* Protease Dose (AU/l) | ΔR (Reflectance Change) |
|---|---|---|
| 0.05 | — | 7.5 |
| 0.1 | — | 10.6 |
| 0.2 | — | 13.1 |
| 0.4 | — | 14.2 |
| 0.6 | — | 16.0 |
| 0.4 | .05 | 16.6 |
| 0.4 | .1 | 18.1 |
| 0.4 | .2 | 19.5 |
| 0.4 | .4 | 20.7 |

EXAMPLE 8

Before use, surface-denatured blood swatches were washed once in detergent to remove whatever could be washed off by detergents alone. Then, the swatches were cut into pieces of 0.5 cm×0.5 cm, and mixed.

200 mg of swatches were placed in test tubes with flat bottoms, and 4 ml of solution (buffer or detergent A or B, see below), with pH 9.5 were added. Then, 2 ml of enzyme solution (see below) were added.

After addition of enzyme, the test tubes were shaken for 30 min. at 25° or 40° C.

After 30 min., the reaction was stopped by addition of 2 ml 10% acetic acid and after another 10 min., filtration through Whatman ® 42 paper filtrate was carried out. The filtrate was analysed by the OPA method described previously in this specification.

The incubation took place in one of the three solutions mentioned below:

(1) Britton and Robinson buffer, pH 9.5.
288 ml of (0.08 mol acetic acid, 0.08 mol phosphoric acid, and 0.08 mol boric acid in 1,000 ml). 600 ml of deionized water, pH is adjusted to 9.5, and then the volume is adjusted to 1,000 ml with deionized water.

(2) and (3) Consisted of the same buffer containing a detergent of the following composition:

|  | Det. A g/l |  | Det. B g/l |  |
| --- | --- | --- | --- | --- |
| Las (Nansa 80S) | 0.40 | g/l | 0.40 | g/l |
| Soap | 0.15 | — | 0.15 | — |
| AE (Berol 065) | 0.15 | — | 0.15 | — |
| STPP | 1.75 | — | 1.75 | — |
| Sodium silicate | 0.40 | — | 0.40 | — |
| CMC | 0.05 | — | 0.05 | — |
| EDTA | 0.01 | — | 0.01 | — |
| Na₂SO₄ | 2.10 | — | 1.00 | — |
| Perborate | — |  | 1.00 | — |
| TAED | — |  | 0.10 | — | pH was adjusted to 9.5.

The enzyme solution contained two proteases (A and B, see below) with a total activity of 0.3 CPU/l, so that the total activity was 0.1 CPU/l after mixing with buffer or detergent. The following activity combinations were used:

| % A | 0 | 50 | 67 | 90 | 100 |
| --- | --- | --- | --- | --- | --- |
| % B | 100 | 50 | 33 | 10 | 0 |

The following protease combinations according to this invention were tested and results are shown in the figures as indicated:

|  | Protease A | Protease B | Temperature |
| --- | --- | --- | --- |
| FIG. 1A | Esperase | Fusarium | 25° C. |
| — 1B | Esperase | Fusarium | 40° C. |
| — 2A | Savinase | Fusarium | 25° C. |
| — 2B | Savinase | Fusarium | 40° C. |
| — 3A | Alcalase | Fusarium | 25° C. |
| — 3B | Alcalase | Fusarium | 40° C. |

The dashed lines in the figures indicate linear interpolations between results with each protease alone.

It is seen that all combinations according to this invention show much better detergency than expected from linear interpolation, even with only 10% of protease B.

For comparison, prior-art combinations were tested in the same way, also at a total activity of 0.3 CPU/l in the enzyme solution and 0.1 CPU/l after mixing with buffer or detergent. The following activity combinations were used:

| % A | 0 | 10 | 50 | 90 | 100 |
| --- | --- | --- | --- | --- | --- |
| % B | 100 | 90 | 50 | 10 | 0 |

Figure 4A:
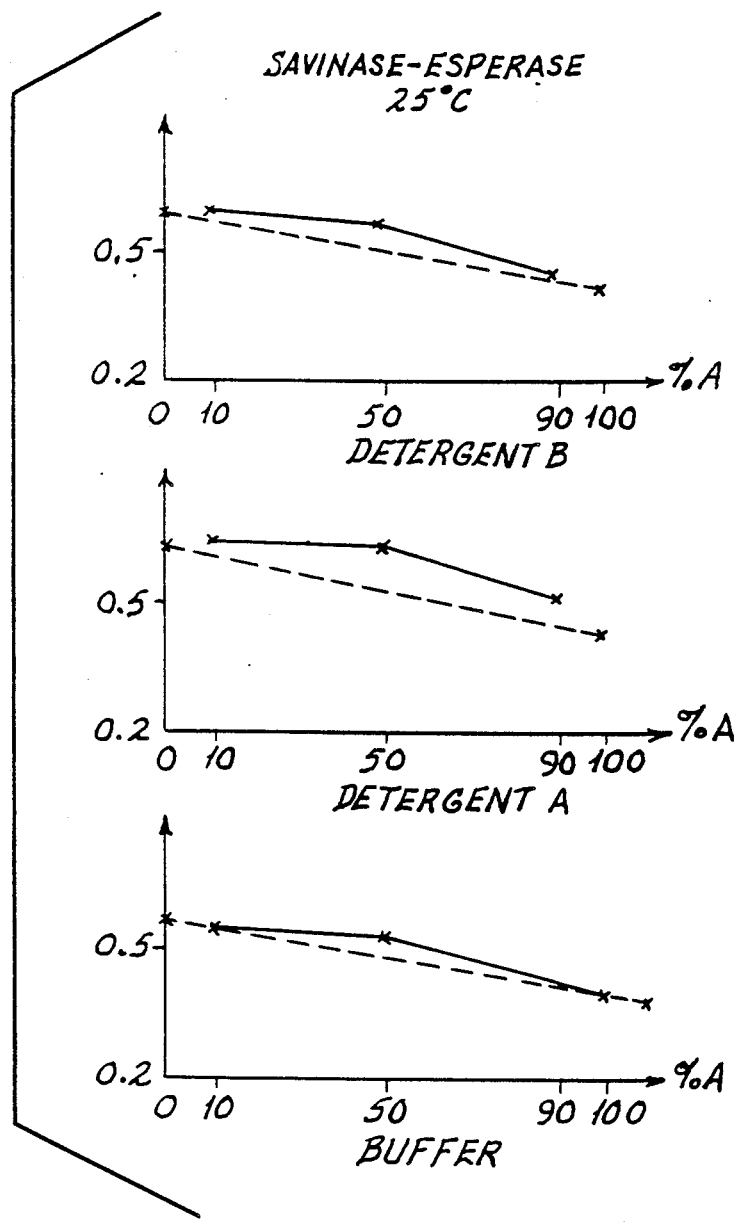
Figure 4B:
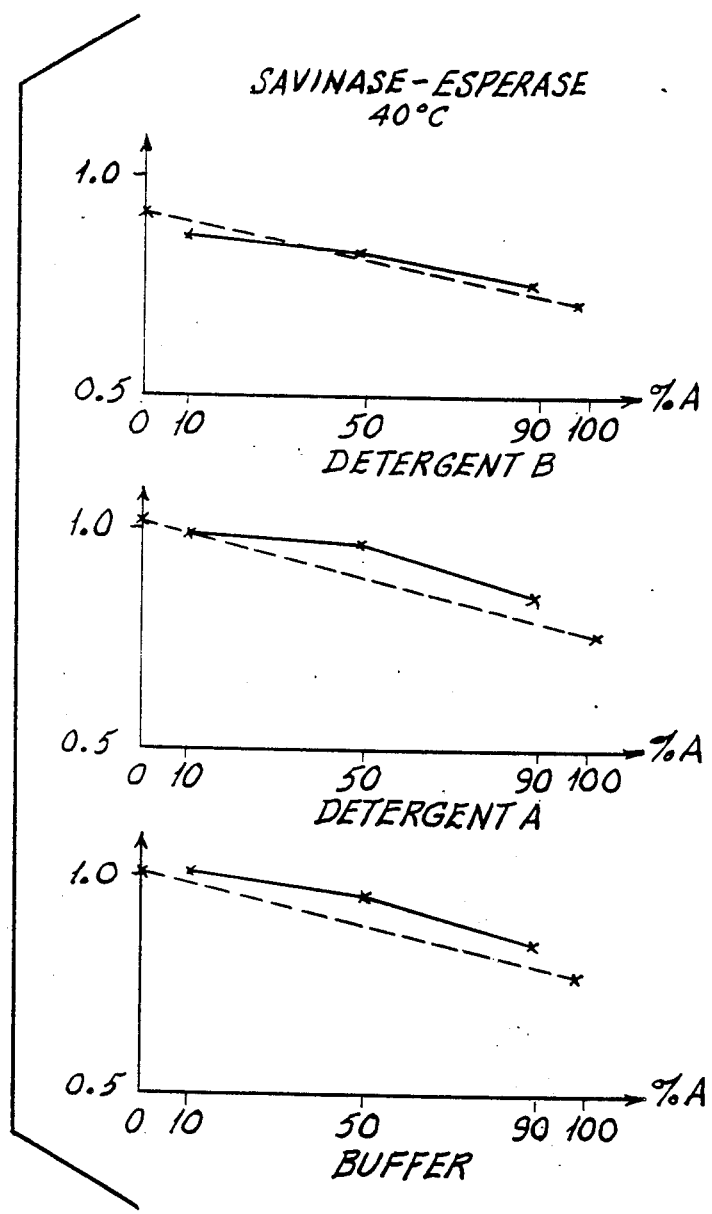
Figure 5A:
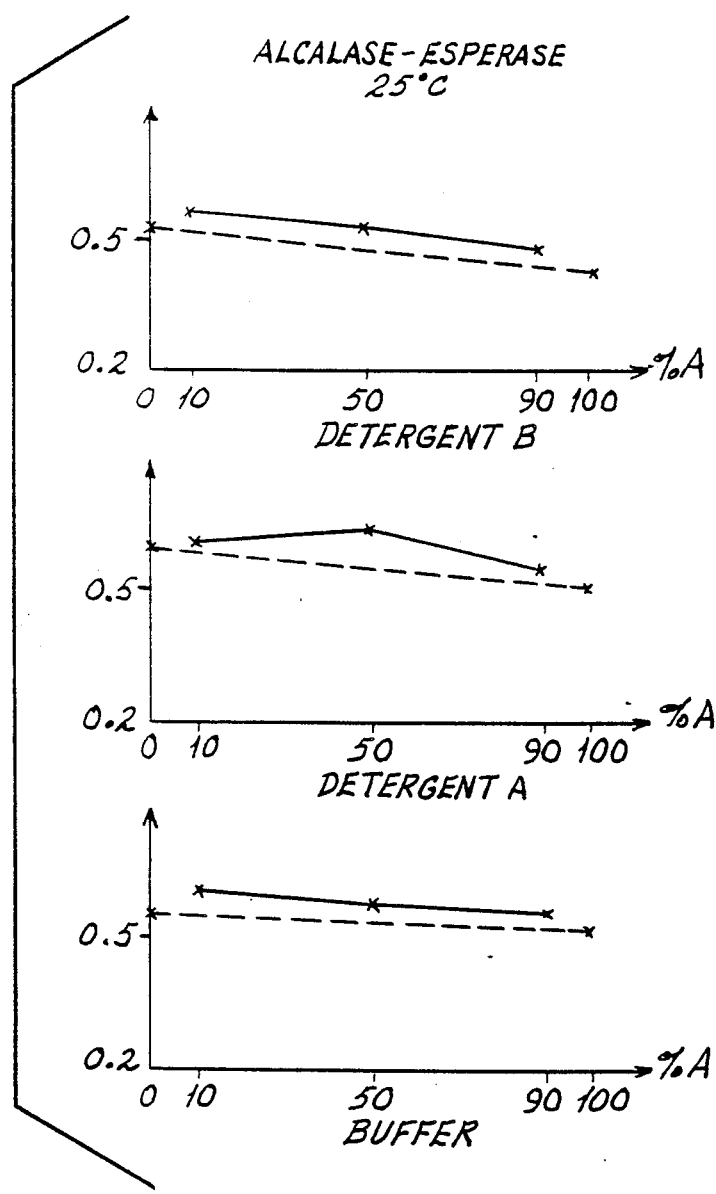

The following prior-art combinations of proteases were tested, and the results are shown in the figures as indicated:

|  | Protease A | Protease B | Temperature |
| --- | --- | --- | --- |
| FIG. 4A | Savinase | Esperase | 25° C. |
| — 4B | Savinase | Esperase | 40° C. |
| — 5A | Alcalase | Esperase | 25° C. |
| — 5B | Alcalase | Esperase | 40° C. |
| — 6A | Alcalase | Savinase | 25° C. |
| — 6B | Alcalase | Savinase | 40° C. |
| — 7A | Maxacal ® | Savinase | 25° C. |
| — 7B | Maxacal ® | Savinase | 40° C. |

Maxacal (Brand name of Gist-Brocades N.V., Netherlands) is an alkaline Bacillus protease.

It is seen that modest improvement of detergency relative to linear interpolation is seen only with some combinations and only at 50% replacement. It is particularly noted that the combination of Savinase and Maxacal shows essentially no improved detergency.

The invention claimed is:

1. A proteolytic detergent additive comprising a combination of at least two alkaline proteases, of which one is a protease obtainable from *Bacillus sp.* and one is a fungal or actinomycete protease the Bacillus protease providing from 50 to 95% of the total proteolytic activity CPU in the detergent additive, the detergent additive comprising a non-dusting granulate or a stabilized liquid having a total protease activity from 0.1 to 10 CPU/g.

2. The detergent additive of claim 1 wherein the Bacillus protease provides from 70 to 95% of the total proteolytic activity CPU.

3. The detergent additive of claim 1, wherein the alkaline proteases have optimum pH above 9 towards casein.

4. The detergent additive of claim 1, comprising a Bacillus protease obtainable from *B. licheniformis*.

5. The detergent additive of claim 1, comprising a Bacillus protease of the serine type, showing optimal proteolytic activity at a pH value above about 9 and retaining 80 to 100 percent of maximum proteolytic activity at pH 12, said activities being measured against hemoglobin by the Anson method.

6. The detergent additive of claim 1, comprising a fungal protease obtainable from *Paecilomyces sp.*

7. The detergent additive of claim 6 comprising a fungal protease obtainable from *P. marquandii*.

8. The detergent additive of claim 1, comprising a fungal protease obtainable from Fusarium sp.

9. The detergent additive of claim 8 comprising a fungal protease obtainable from *Fusarium oxysporum*.

10. The detergent additive of claim 1, comprising an actinomycete protease obtainable from *Nocardiopsis sp.*

11. The detergent additive of claim 10 comprising an actinomycete protease obtainable from *N. dassonvillei*.

12. A detergent composition containing therein a proteolytic detergent additive which comprises a combination of at least two alkaline proteases, of which one is a protease obtainable from a *Bacillus sp.* and one is a fungal or actinomycete protease, the Bacillus protease providing from 50 to 95% of the total proteolytic activity CPU in the detergent additive, the detergent additive comprising a non-dusting granulate or a stabilized liquid having a total protease activity from 0.1 to 10 CPU/g.

13. The composition of claim 12, characterized by a total protease activity between 0.001 and 0.08 CPU/g.

14. A washing process which comprises contacting soiled solid materials in an aqueous bath with a detergent composition containing therein a proteolytic detergent additive comprising a combination of at least two alkaline proteases, of which one is a protease obtainable from *Bacillus sp.* and one is a fungal or actinomycete protease, the Bacillus protease providing from 50 to 95% of the total proteolytic activity CPU in detergent additive, the detergent additive comprising a non-dusting granulate or a stabilized liquid having a total protease activity from 0.1 to 10 CPU/g.

* * * * *